(12) United States Patent
Souda et al.

(10) Patent No.: US 7,652,170 B2
(45) Date of Patent: Jan. 26, 2010

(54) METHOD FOR PRODUCING PRIMARY AMINE COMPOUND

(75) Inventors: Hiroshi Souda, Oita (JP); Naoyuki Takano, Ibaraki (JP); Shinzo Seko, Toyonaka (JP)

(73) Assignee: Sumitomo Chemical Company, Limited, Tokyo (JP)

( * ) Notice: Subject to any disclaimer, the term of this patent is extended or adjusted under 35 U.S.C. 154(b) by 35 days.

(21) Appl. No.: 12/097,974

(22) PCT Filed: Dec. 25, 2006

(86) PCT No.: PCT/JP2006/325752

§ 371 (c)(1),
(2), (4) Date: Jun. 18, 2008

(87) PCT Pub. No.: WO2007/074762

PCT Pub. Date: Jul. 5, 2007

(65) Prior Publication Data

US 2009/0287023 A1   Nov. 19, 2009

(30) Foreign Application Priority Data

Dec. 26, 2005   (JP) .............................. 2005-371743

(51) Int. Cl.
  *C07C 209/08* (2006.01)
(52) U.S. Cl. .................. 564/376; 564/375; 564/481; 564/483; 564/484
(58) Field of Classification Search .................. None
See application file for complete search history.

(56) References Cited

U.S. PATENT DOCUMENTS 5,756,769 A * 5/1998 Seko et al. .................. 549/74
2007/0197803 A1   8/2007 Takano et al.

FOREIGN PATENT DOCUMENTS

| JP | 45-34127 B | 11/1970 |
|----|------------|---------|
| JP | 62-161765 A | 7/1987 |
| JP | 2002-212148 A | 7/2002 |
| WO | WO-2006/109811 A1 | 10/2006 |

OTHER PUBLICATIONS

Saljoughian, M. et al., "Specific Labelling of Putrescine Dihydrochloride by Heterogeneous Hydrogenation with Deuterium or Tritium Gas in Dimethyl Sulfoxide." Journal of Labelled Compounds and Radiopharmaceuticals—vol. XXV, No. 3, 1988, pp. 313-328. XP-002509761.
M. S. Gibson, et al., The Gabriel Synthesis of Primary Amines, Angew. Chem. Internat. Edit., vol. 7, 1968, pp. 919-930.
Han Yinglin, et al., A Convenient Synthesis of Primary Amines Using Sodium Diformylamide as A Modified Gabriel Reagent, Synthesis, 1990, pp. 122-124.
Nikola Blazevic, et al., Hexamethylenetetramine, A Versatile Reagent in Organic Synthesis, Synthesis, 1979, pp. 161-176.
Patent Abstracts of Japan, JP-62-161765-A, published Jul. 17, 1987.
Patent Abstracts of Japan, JP-2002-212148-A, published Jul. 31, 2002.
Jean Jacques, Bull. Soc. Chim., 1945, vol. 12, pp. 843-845.
Ronald M. Magid, et al., "Improvements in the Hexachloroacetone/Triphenylphosphine Procedure for the Conversion of Allylic Alcohols into Chlorides", J. Org. Chem., 1981, vol. 46, pp. 824-825.
Shuki Araki, et al., "Regio-and Stereoselective Conversion of Allylic Alcohols to Halides via Allylic Phosphates", Synthesis, 1984, pp. 841-842.

(Continued)

*Primary Examiner*—Brian J Davis
(74) *Attorney, Agent, or Firm*—Birch, Stewart, Kolasch & Birch, LLP

(57) ABSTRACT

Disclosed is a method for producing a primary amine compound represented by the formula (2) below, which is characterized in that a halogen compound represented by the formula (1) below, ammonia and formaldehyde are reacted with each other, and then the thus-obtained reaction product is [1] brought into contact with an aqueous solution of an acid or [2] reacted with a hydroxylamine under acidic conditions. By this method, a primary amine compound can be commercially advantageously produced by using a low-cost ammonia while suppressing production of a secondary amine as a by-product. (1) (In the formula, $R^1$ and $R^2$ independently represent a hydrogen atom, a C1-C5 alkyl group which may be substituted by a halogen atom or the like, a C1-C5 alkoxy group which may be substituted by a halogen atom, a cyano group, a C2-C11 alkenyl group or a phenyl group or the like; $R^3$ represents a hydrogen atom, a linear or branched C1-C5 alkyl group or a cyano group; and X represents a halogen atom.) (2) (In the formula, $R^1$, $R^2$ and $R^3$ are as defined above.)

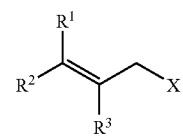

(1)

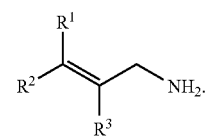

(2)

9 Claims, No Drawings

OTHER PUBLICATIONS

Svante Brandänge, et al., "A Convenient Route to 3-Pyrroline Utilizing the Delépine Reaction", Synthesis, 1988, pp. 347-348.

MaoJun Guo, et al., "Synthesis of 4-pentenoic and 5-hexenoic acids on polystyrene resin and their use as cleavable linkers", Tetrahedron Letters, 2002, vol. 43 (No. 32), pp. 5611-5615.

Zhixing Wu, et al., "Design, Synthesis, and Structure-Activity Relationships of Haloenol Lactones: Site-Directed and Isozyme-Selective Glutathione S-Transferase Inhibitors", J. Med. Chem., 2004, vol. 47, pp. 3282-3294.

* cited by examiner

METHOD FOR PRODUCING PRIMARY AMINE COMPOUND

This application is a 371 of PCT/JP2006/325752 filed Dec. 25, 2006.

TECHNICAL FIELD

The present invention relates to a method for producing a primary amine compound.

BACKGROUND ART

There have been many reports concerning selective synthetic methods of primary amines from of old, and examples of known methods include Gabriel reaction (for example, non-Patent Document 1) using phthalimide and related reactions (for example, non-Patent Document 2), Delepine reaction (for example, non-Patent Document 3) using hexamethylenetetramine, and the like. However, all of these methods are not necessarily satisfactory from the industrial point of view because these methods use expensive amination agents and include complicated decomposition operations. On the other hand, methods using inexpensive ammonia as an amination agent are industrially useful. However, these methods have difficulties in suppressing formation of secondary amines and tertiary amines and therefore, primary amines could not be selectively obtained (Patent Document 1). Under these circumstances, a method is known for selective producing a primary amine in the presence of an aromatic aldehyde (Patent Document 2). It is however necessary to recover the aromatic aldehyde separately and therefore, this method is not necessarily satisfactory.

non-Patent Document 1: Angew. Chem. Int. Ed. Engl., (1968), Vol. 7, p 919 (1968)

non-Patent Document 2: Synthesis, 1990, p 122 non-Patent Document 3: Synthesis, 1979, p 161

Patent Document 1: JP 45-34127 B

Patent Document 2: JP 2002-212148 A

DISCLOSURE OF THE INVENTION

Problems to be Solved by the Invention

Under these circumstances, the present inventors have studied to develop a method for producing a primary amine more industrially advantageously by using inexpensive ammonia while suppressing formation of secondary amines and tertiary amines as byproducts. As a result, the present inventors have found that an intended primary amine compound can be produced by reacting a halogen compound, ammonia and formaldehyde which is inexpensive and easily available, and subjecting the resultant product to a decomposition treatment. Thus, the present invention has been completed.

Means to Solve the Problem

That is, the present invention provides a method for producing a primary amine compound represented by the formula (2):

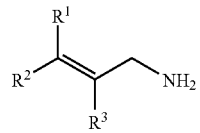

wherein $R^1$ and $R^2$ each independently represents a hydrogen atom, a straight-chain or branched C1-C5 alkyl group which may be substituted with a halogen atom, a monoalkylamino group, a di(alkyl)amino group or an amino group, a straight-chain or branched C1-C5 alkoxy group which may be substituted with a halogen atom, a cyano group, a straight-chain or branched C2-C11 alkenyl group, a straight-chain or branched C2-C11 alkynyl group, or a phenyl group which may be substituted with 1 to 3 substituents selected from the group consisting of a halogen atom, a straight-chain or branched C1-C5 alkyl group, a straight-chain or branched C1-C5 alkoxy group, a cyano group, a nitro group and C1-C3 alkylenedioxy group, and $R^3$ represents a hydrogen atom, a straight-chain or branched C1-C5 alkyl group or a cyano group;

which comprises reacting a halogen compound represented by the formula (1):

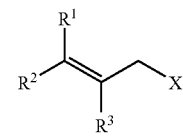

wherein $R^1$, $R^2$ and $R^3$ are the same as above and X represents a halogen atom, with ammonia and formaldehyde, and then 1) bringing the thus-obtained reaction product into contact with an aqueous solution of an acid, or 2) reacting the reaction product with a hydroxylamine under acidic conditions.

EFFECT OF THE INVENTION

According to the present invention, a primary amine compound can be produced selectively and industrially advantageously from a halogen compound and ammonia.

BEST MODE FOR CARRYING OUT THE INVENTION

Hereinafter, the present invention will be illustrated in detail.

The substituents $R^1$, $R^2$ and $R^3$ of the halogen compound (1) used in the production of the primary amine compound (2) of the present invention will be described below.

Examples of the straight-chain or branched C1-C5 alkyl group represented by the substituent $R^1$ or $R^2$ include a methyl group, an ethyl group, an n-propyl group, an i-propyl group, an n-butyl group, an s-butyl group, an i-butyl group, a t-butyl group, a pentyl group, an i-pentyl group and a neo-pentyl group. These straight-chain or branched C1-C5 alkyl groups may be substituted with a monoalkylamino group such as a methylamino group or an ethylamino group, a di(alkyl)amino group such as a dimethylamino group or a diethylamino group or an amino group. Examples of the alkyl group which may be bound to the nitrogen atom of the amino group include the same C1-C5 alkyl groups as those mentioned above.

Examples of the straight-chain or branched C1-C5 alkoxy group represented by the substituent $R^1$ or $R^2$ include a methoxy group, an ethoxy group, an n-propoxy group, an i-propoxy group, an n-butoxy group, an s-butoxy group, an i-butoxy group, a t-butoxy group, a pentyloxy group, an i-pentyloxy group and a neo-pentyloxy group.

These straight-chain or branched C1-C5 alkyl or straight-chain or branched C1-C5 alkoxy groups may be substituted with a halogen atom. Examples of the halogen atom include fluorine, chlorine and bromine.

Examples of the straight-chain or branched C2-C11 alkenyl group represented by the substituent $R^1$ or $R^2$ include a vinyl group, a propenyl group, a 2-methylpropenyl group, a butenyl group, a 1,3-butadienyl group, a 1,5-hexadienyl group, a 2,6-dimethyl-1,5-heptadienyl group and a 4,8-dimethyl-3,7-nonadienyl group.

Examples of the straight-chain or branched C2-C11 alkynyl group represented by the substituent $R^1$ or $R^2$ include an ethynyl group, a propynyl group, a butynyl group, a 3-methylbutynyl group and a 3,3-dimethylbutynyl group.

Examples of the straight-chain or branched C1-C5 alkyl group and a straight-chain or branched C1-C5 alkoxy group of the phenyl group which may be substituted with 1 to 3 substituents selected from the group consisting of a halogen atom, a straight-chain or branched C1-C5 alkyl group, a straight-chain or branched C1-C5 alkoxy group, a cyano group, a nitro group and a C1-C3 alkylenedioxy group represented by the substituent $R^1$ or $R^2$ include the same groups as mentioned above.

Examples of C1-C3 alkylenedioxy group include a methylenedioxy group, an ethylenedioxy group and a trimethylenedioxy group.

Examples of the straight-chain or branched C1-C5 alkyl group represented by $R^3$ include the same groups as those exemplified with respect to the straight-chain or branched C1-C5 alkyl group represented by the substituent $R^1$ or $R^2$.

Preferably, $R^1$ and $R^2$ are independently a hydrogen atom, a straight-chain or branched C1-C5 alkyl group, a straight-chain or branched C1-C5 alkoxy group, a straight-chain or branched C2-C11 alkenyl group, a straight-chain or branched C2-C11 alkynyl group or a phenyl group which may be substituted with 1 to 3 substituents selected from the group consisting of a halogen atom, a straight-chain or branched C1-C8 alkyl group, a straight-chain or branched C1-C5 alkoxy group, a nitro group and a C1-C3 alkylenedioxy group.

$R^3$ is preferably a hydrogen atom or a straight-chain or branched C1-C5 alkyl group.

As $R^1$ and $R^2$, a hydrogen atom, a methyl group or a phenyl group is more preferable.

As $R^3$, a hydrogen atom or a methyl group is more preferable.

Examples of the halogen atom represented by X include a chlorine atom, a bromine atom and an iodine atom.

Examples of the halogen compound (1) include allyl chloride, crotyl chloride, methallyl chloride, geranyl chloride, 1-chloro-3-methyl-2-butene, 1-chloro-2-pentene, 1-chloro-2-hexene, 1-chloro-3-methyl-2-pentene, 1-chloro-4-methoxy-2-butene, 1,4-dichloro-2-butene, 4-chloro-2-butenylamine, 2-(2-chloro-ethylidene)-malononitrile, (4-chloro-2-butenyl)-dimethylamine, (4-chloro-2-butenyl)-diethylamine, 1-chloro-2-methyl-2-butene, 4-chloro-1,1,1-trifluoro-2-butene, 1-chloro-2-methyl-2-pentene, 1-chloro-3, 7,11-trimethyl-2,6,10-dodecatriene, 1-chloro-6,6-dimethyl-2-heptene-4-yn, cinnamyl chloride, 1-chloro-4-(3-chloropropenyl)-benzene, 1-chloro-3-(3-chloropropenyl)-benzene, 1-(3-chloropropenyl)-4-methoxybenzene, 1-(3-chloropropenyl)-3-methoxybenzene, 1-(3-chloropropenyl) 3-methylbenzene, (4-(3-chloropropenyl)-phenyl)dimethylamine, 4-(3-chloropropenyl)-1,2-dimethoxybenzene, 4-(3-chloropropenyl)-benzonitrile, 1-(3-chloropropenyl)-3-nitrobenzene and 5-(3-chloropropenyl)-3-benzo[1,3]dioxol and compounds obtained by substituting a bromine atom or an iodine atom for a chlorine atom of the allyl moiety of the above compounds.

Preferable examples of the halogen compound (1) include allyl chloride, crotyl chloride, methallyl chloride, geranyl chloride, 1-chloro-3-methyl-2-butene, cinnamyl chloride, allyl bromide and cinnamyl bromide.

The halogen compound (1) is commercially available, or available by, for example, methods described in "Bull. Soc. Chim.)", 1945, vol. 12, p. 843, "J. Org. Chem.)", 1981; vol. 46, p. 824, "Synthesis", 1984, p. 841, "Synthesis", 1988, p. 347, "Tetrahedron Letters", 2002, vol. 43 (No. 32), p. 5611, and "J. Med. Chem.", 2004, vol. 47, p3282 or modification of these methods.

As ammonia, ammonia gas or liquid ammonia can be used. Further, aqueous ammonia can be used and, for example, an organic solvent solution of ammonia obtained by dissolving ammonia in an organic solvent capable of dissolving ammonia such as methanol can also be used.

The amount of ammonia to be used is usually 1 to 30 mol, preferably 2 to 25 mol and more preferably 2 to 10 mol based on 1 mol of the halogen compound (1).

It is preferable to use paraformaldehyde or formalin as the above formaldehyde from the viewpoint of handling properties though formaldehyde gas can be used. The amount of formaldehyde to be used is usually 1 to 10 mol, preferably 1 to 8 mol and more preferably 1 to 5 mol based on 1 mol of the halogen compound (1). The amount of ammonia to be used based on the halogen compound (1) is preferably larger than that of formaldehyde.

The reaction temperature is usually 15 to 100° C. and preferably 20 to 90° C. The reaction is carried out at atmospheric or under pressurized pressure though there is no specific limitation to the reaction pressure. As a reactor, in order to prevent effusion of ammonia out of the reaction system, a pressure reactor for carrying out the reaction in a sealed system is preferably used though the reactor is not limited thereto.

The reaction is preferably carried out in a solvent though it can be carried out without a solvent. Any solvent can be used as this solvent as far as it is inert in the reaction of the present invention. Examples of the solvent include alcohol type solvents such as methanol, ethanol, n-propanol isopropanol or the like, aromatic hydrocarbon type solvents such as toluene, xylene or the like, halogenated hydrocarbon type solvents such as chlorobenzene, dichlorobenzene or the like, aliphatic hydrocarbon solvents such as hexane, heptane, cyclohexane or the like, ether type solvents such as diethyl ether, tetrahydrofuran, dioxane or the like, aprotic polar solvents such as acetonitrile, propionitrile, dimethylsulfoxide, N,N-dimethylacetamide or the like, and water. These solvents can be used alone or as a mixture thereof. Among these solvents, an alcohol type solvent or water is preferable, and an alcohol type solvent is more preferable. The amount of the solvent to be used is usually 1 to 10 parts by weight based on 1 part by weight of the halogen compound (1).

The reaction is carried out by mixing the halogen compound (1), ammonia and formaldehyde, and bringing them into contact with each other. The order of mixing is not specifically limited. For example, the halogen compound (1), ammonia and formaldehyde can be mixed to react at a predetermined temperature, or the halogen compound (1) can be mixed with formaldehyde in advance and ammonia is added to the mixture to react them. Further, ammonia can be mixed with formaldehyde in advance and the halogen compound (1) is added to the mixture to react them. Furthermore, the halogen compound (1) and ammonia are added simultaneously to formaldehyde to carry out the reaction, or the halogen compound (1) and formaldehyde can be simultaneously added to ammonia to carry out the reaction.

When the halogen compound (1) has a substituent such as an amino group, an alkylamino group or a dialkylamino group, it can be used in the reaction in the form of a salt which is an acid adduct of the halogen compound (1) (for example, a hydrochloride).

In addition, if necessary, the reaction can be carried out in the presence of a phase transfer catalyst, for example, including a quaternary ammonium salt such as triethylbenzylammonium chloride, tri-n-octylmethylammonium chloride, tri-methyldecyldecylammonium chloride, tetramethylammonium bromide, tetra-n-butylammonium bromide, or the like, and crown ether or the like.

According to this reaction, a reaction product containing a methyleneimine compound represented by the following formula (3):

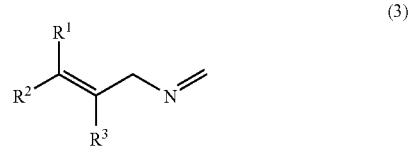

(3)

wherein $R^1$, $R^2$ and $R^3$ are as defined above, can be obtained.

Then, the steps for producing the primary amine compound represented by the formula (2) (hereinafter abbreviated as the primary amine compound (2)) will be illustrated. In the steps, the reaction product containing the methyleneimine compound (3) 1) is brought into contact with an aqueous acid solution or 2) is reacted with hydroxylamine under acidic conditions to produce the primary amine compound (2).

First, a step of 1) bringing the reaction product containing the methyleneimine compound (3) into contact with an aqueous acid solution will be described.

In this step, the reaction product containing the methyleneimine compound (3) obtained in the previous step is brought into contact with an aqueous acid solution to convert it into the primary amine compound (2) and this step is usually carried out by bringing the reaction product containing the methyleneimine compound (3) into contact with an aqueous acid solution and mixing them. Examples of the aqueous acid solution include aqueous solutions of hydrochloric acid, sulfuric acid, phosphoric acid and nitric acid. Among these aqueous solutions, aqueous solutions of hydrochloric acid and sulfuric acid are preferable, but there is no particular limitation to the acid concentration of the aqueous acid solution. Further, the amount of the acid to be used is usually 1 to 10 mol, preferably 1 to 5 mol based on 1 mol of the halogen compound (1) charged as the starting material of the reaction.

This step can be carried out after the reaction product containing the methyleneimine compound (3) produced in the previous step is isolated from the reaction mixture or directly without isolation of the reaction product containing the methyleneimine compound (3) or after it is extracted with an organic layer.

The contact of the methyleneimine compound (3) with the aqueous acid solution is usually carried out at 10 to 100° C., preferably 25 to 70° C.

The contact between the reaction product containing the methyleneimine compound (3) and the acid brings about a progress in hydrolysis of the reaction product containing the methyleneimine compound (3), thereby forming formaldehyde as a by-product. In order to facilitate the removal of formaldehyde formed as a by-product, the reaction product containing the methyleneimine compound (3) is preferably brought into contact with the aqueous acid solution in the presence of a lower alcohol compound to carry out the hydrolysis treatment of the reaction product containing the methyleneimine compound (3) while converting the by-produced formaldehyde into an acetal compound. Examples of the lower alcohol compound include lower alcohol compounds having 1 to 4 carbon atoms such as methanol, ethanol, propanol and butanol. The amount of the alcohol to be used is usually 1.5 mol or more, preferably 2 mol or more, and more preferably 2.5 mol or more based on 1 mol of the halogen compound (1) charged as the starting material of the reaction, and there is no particular limitation to the upper limit of this amount. When the reaction solution containing the methyleneimine compound (3) is used as it is and such a lower alcohol compound is present in the reaction mixture, the amount of the lower alcohol compound can be determined in consideration of the amount of the lower alcohol contained in the reaction mixture.

Further, there is the case where formaldehyde is also remained in the reaction mixture. In this case, it is necessary to use a lower alcohol in an amount enough to convert not only by-produced formaldehyde but also formaldehyde remained in the reaction mixture into an acetal compound. Of course, formaldehyde can be converted into an acetal compound after the reaction product containing the methyleneimine compound (3) is hydrolyzed.

After completion of the hydrolysis treatment, for example, the primary amine compound (2) or its acid addition salt can be isolated by carrying out a concentration treatment. The isolated compound can be purified by recrystallization if necessary. Further, the primary amine compound (2) can also be isolated by, after the concentrating treatment, carrying out an extraction treatment with addition of alkali water and a hydrophobic organic solvent and concentrating the resulting organic layer. The isolated primary amine compound can be purified by distillation or column chromatography if necessary. Examples of the alkali water include aqueous alkali metal hydroxide solutions such as an aqueous sodium hydroxide solution. As to the amount of the aqueous alkali solution, the solution is used in such an amount that the aqueous layer of the extraction treatment is adjusted to pH ranging usually from 8 to 14, preferably from 10 to 14.

Next, the step of reacting hydroxylamine with the reaction product containing the methyleneimine compound (3) under acidic conditions (hereinafter abbreviated as the "hydroxylamine treating step") will be described.

This step is usually carried out by bringing the reaction product containing the methyleneimine compound (3) into contact with hydroxylamine under acidic conditions and mixing them.

As hydroxylamine, free hydroxylamine can be used. Alternatively, an acid addition salt such as a hydrochloride of hydroxylamine ($NH_2OH.HCl$) and a sulfate of hydroxylamine ($(NH_2OH)_2.H_2SO_4$) can be used. Usually, commercially available hydroxylamine is used. Further, hydroxylamine can be used as it is or in the form of a solution, for example, an aqueous solution.

The amount of hydroxylamine to be used is usually 1 to 30 mol, preferably 1 to 15 mol and more preferably 1 to 10 mol based on 1 mol of the halogen compound (1) charged as the starting material or the reaction.

The reaction product containing the methyleneimine compound (3) and hydroxylamine are usually brought into contact with each other and mixed with each other in an aqueous solvent or a mixture of solvents containing water and an organic solvent under acidic conditions. The amount of water or the mixture of solvents containing water and an organic solvent is usually 1 to 40 parts by weight based on 1 part by weight of the halogen compound (1) charged as the starting material of the reaction. There is no particular limitation to the ratio of water to the organic solvent when the mixture of solvents of water and the organic solvent is used. Examples of the organic solvent include aromatic hydrocarbon type solvents such as toluene, xylene or the like, halogenated hydrocarbon type solvents such as chlorobenzene, dichlorobenzene or the like, and ether type solvents such as diethyl ethers diisopropyl ether, methyl tert-butyl ether, tetrahydrofuran or the like, and alcohol type solvents such as methanol, ethanol, isopropanol or the like.

Examples of the acid used when hydroxylamine is reacted under acidic conditions include mineral acids such as hydrochloric acid, sulfuric acid, phosphoric acid or the like, and organic carboxylic acids such as acetic acid, propionic acid, citric acid or the like. Among these acids, mineral acids are preferable, and hydrochloric acid and sulfuric acid are more preferable. There is no specific limitation to the amount of the acid to be used as long as hydroxylamine and the reaction product containing the methyleneimine compound (3) are brought into contact and mixed with each other under acidic conditions.

Hydroxylamine can be added to the reaction product containing the methyleneimine compound (3), or the reaction product containing the methyleneimine compound (3) can be added to hydroxylamine.

The temperature at which hydroxylamine is reacted is usually 0 to 100° C., preferably 0 to 50° C.

When hydroxylamine is reacted with the reaction product containing the methyleneimine compound (3) under acidic conditions, formaldoxime or its trimer is formed by the reaction of the reacted hydroxylamine with formaldehyde together with the acid addition salt of the primary amine compound (2). Therefore, for example, a base and, if necessary, a hydrophobic organic solvent are preferably added to the above solution containing the acid addition salt of the primary amine compound (2) to carry out an extraction treatment under basic conditions, thereby separating an organic layer containing the primary amine compound (2) from an aqueous layer containing formaidoxime or its trimer. Then, the obtained organic layer can be concentrated to isolate the primary amine compound (2) having a higher purity. The isolated primary amine compound (2) can be converted into an acid addition salt such as a hydrochloride by reacting the primary amine compound (2) with an acid, for example, hydrochloric acid. Examples of the base include alkali metal hydroxides such as sodium hydroxide or the like. These alkali metal hydroxides can be used in such an amount that the aqueous layer of the extraction treatment is adjusted to pH range from 8 to 14, preferably 10 to 14. Examples of the hydrophobic organic solvent include aromatic hydrocarbon type solvents such as toluene and xylene, halogenated hydrocarbon type solvents such as chlorobenzene, dichlorobenzene or the like, ester type solvents such as ethyl acetate, butyl acetate or the like, and ketone type solvents such as methyl ethyl ketone, methyl isobutyl ketone or the like, which can be used alone or as a mixture thereof. The amount thereof is not specifically limited.

Further, the organic layer containing the primary amine compound (2) obtained in the above extraction treatment is mixed with an aqueous acid solution and then, separated into layers to obtain an aqueous solution containing an acid addition salt of the primary amine compound (2). Then, the acid addition salt of the primary amine compound (2) can be isolated from the aqueous solution as it is or after the solution is partly concentrated. Further, an insufficient solvent which scarcely dissolves the acid addition salt of the primary amine compound (2) can be added to an aqueous solution containing the acid addition salt of the primary amine compound (2) to precipitate crystals of the acid addition salt of the primary amine compound (2). Examples of the aqueous acid solution include aqueous solutions of acids such as hydrochloric acid, sulfuric acid, acetic acid, methanesulfonic acid or the like. As to the amount of the aqueous acid solution, these acid solutions are used in such an amount that the aqueous layer of the extraction treatment is adjusted to pH generally in the range from 0.1 to 5.5, preferably 3 to 5. When the aqueous solution containing the acid addition salt of the primary amine compound (2) is colored, a decoloring agent, for example, activated carbon can be added to the aqueous solution to carry out a decoloring treatment.

Examples of the primary amine compound (2) thus obtained include allylamine, crotylamine, methallylamine, geranylamine, 3-methyl-2-butenylamine, 2-pentenylamine, 2-hexenylamine, 3-methyl-2-pentenylamine, 4-methoxy-2-butenylamine, 4-chloro-2-butenylamine, 2-butene-1,4-diamine, 2-(2-amino-ethylidene)-malononitrile, N,N-dimethyl-2-butene-1,4-diamine, N,N-diethyl-2-butene-1,4-diamine, 2-methyl-2-butenylamine, 4,4,4,-trifluoro-2-butenylamine, 2-methyl-2-pentenylamine, 3,7,11-trimethyl-2,6,10-dodecatrienylamine, 6,6-dimethyl-2-heptene-4-ynylamine, cinnamylamine, 3-(4-chlorophenyl)-allylamine, 3-(3-chlorophenyl)-allylamine, 3-(4-methoxyphenyl)-allylamine, 3-(3-methoxyphenyl)-allylamine, 3-m-tolyl-allylamine, (4-(3-aminopropenyl)-phenyl)dimethylamine, 3-(3, 4-dimethoxyphenyl)-allylamine, 4-(3-aminopropenyl) benzonitrile, 3-(3-nitrophenyl)-allylamine and 3-(5-benzo[1, 3]dioxazolyl)-allylamine.

The present invention will be illustrated in more detail by way of examples, which, however, are not intended to be limiting of the present invention. For the analysis, a gas chromatography (GC) method and a high-performance liquid chromatography (LC) method were used.

EXAMPLE 1

A stainless autoclave was charged with 3.91 parts by weight of allyl chloride (content: 98% by weight), 4.89 parts by weight of parafommaldehyde (content: 92% by weight) and 28.4 parts by weight of an aqueous 12 wt % ammonia/methanol solution, and the mixture was stirred at 40° C. for 3 hours, at 50° C. for 2 hours, and further at 70° C. for 1 hour to react them. To the reaction mixture were added 51.3 parts by weight of an aqueous 24 wt % hydroxylamine sulfate solution and 22.7 parts by weight of 35 wt % sulfuric acid to adjust the solution to pH 0.8, followed by stirring at 40° C. for 30 minutes. Then, 61.3 parts by weight of an aqueous 27 wt % sodium hydroxide solution was added to the solution to adjust the solution to pH 13. When the mixture obtained was analyzed, the yield of allylamine was 87.8%, the yield of diallylamine was 3.5%, and the yield of triallylamine was 1.2% (GC method, based on allyl chloride).

COMPARATIVE EXAMPLE 1

According to a similar manner as that in Example 1, the reaction was carried out except that no paraformaldehyde was charged. When the reaction mixture was analyzed, the yield of allylamine was 26.7%, the yield of diallylamine was 11.8%, and the yield of triallylamine was 14.1% (GC method, based on allyl chloride).

EXAMPLE 2

A stainless autoclave was charged with 8.70 parts by weight of cinnamyl chloride (content: 99% by weight), 5.59 parts by weight of paraformaldehyde (content: 92% by weight) and 35.22 parts by weight of a 12 wt % ammonia/methanol solution, and the mixture was stirred at 70° C. for 4 hours to react them. The reaction mixture was subjected to a post-treatment under similar conditions as those of Example 1. When the mixture thus obtained was analyzed, the yield of cinnamylamine was 72.8%, the yield of bis-(cinnamyl)amine was 18.9%, and the yield of tris-(cinnamyl)amine was 8.1% (LC method, based on cinnamyl chloride).

COMPARATIVE EXAMPLE 2

According to a similar manner as that of Example 2, the reaction was carried out except that no paraformaldehyde was charged. When the reaction mixture was analyzed, the yield of cinnamylamine was 11.6%, the yield of bis-(cinnamyl)amine was 9.1%, and the yield of tris-(cinnamyl)amine was 4.2% (LC method, based on cinnamyl chloride).

INDUSTRIAL APPLICABILITY

According to the present invention, a method for producing a primary amine compound which is highly selective and industrially advantageous can be provided.

The invention claimed is:

1. A method for producing a primary amine compound represented by the formula (2):

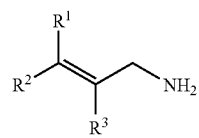

(2)

wherein $R^1$ and $R^2$ each independently represents a hydrogen atom,
a straight-chain or branched C1-C5 alkyl group which may be substituted with a halogen atom, a monoalkylamino group, a di(alkyl)amino group or an amino group,
a straight-chain or branched C1-C5 alkoxy group which may be substituted with a halogen atom,
a cyano group,
a straight-chain or branched C2-C11 alkenyl group,
a straight-chain or branched C2-C11 alkynyl group, or
a phenyl group which may be substituted with 1 to 3 substituents selected from the group consisting of a halogen atom, a straight-chain or branched C1-C5 alkyl group, a straight-chain or branched C1-C5 alkoxy group, a cyano group, a nitro group and C1-C3 alkylenedioxy group, and
$R^3$ represents a hydrogen atom, a straight-chain or branched C1-C5 alkyl group or a cyano group;
which comprises reacting a halogen compound represented by the formula (1):

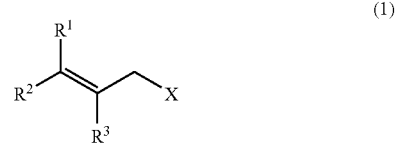

(1)

wherein $R^1$, $R^2$ and $R^3$ are the same as above and X represents a halogen atom, with ammonia and formaldehyde, and then 1) bringing the thus-obtained reaction product into contact with an aqueous solution of an acid, or 2) reacting the reaction product with a hydroxylamine under acidic conditions.

2. The method according to claim 1, wherein an amount of formaldehyde to be used is 1 to 10 mol based on 1 mol of the halogen compound represented by the formula (1).

3. The method according to claim 1 or 2, wherein the formaldehyde is paraformaldehyde or formalin.

4. The method according to any one of claims 1 to 3, wherein an amount of ammonia to be used is 1 to 30 mol based on 1 mol of the halogen compound represented by the formula (1).

5. The method according to any one of claims 1 to 4, wherein the reaction product is brought into contact with the aqueous acid solution in the presence of a lower alcohol compound.

6. The method according to any one of claims 1 to 4, wherein an amount of hydroxylamine to be used is 1 to 10 mol based on 1 mol of the halogen compound represented by the formula (1).

7. The method according to claim 6, which further comprises a step of extracting a mixture obtained by reaction of hydroxylamine with the reaction product with a hydrophobic organic solvent under basic conditions to separate an organic layer containing the primary amine compound represented by the formula (2).

8. The method according to any one of claims 1 to 7, wherein $R^1$ and $R^2$ respectively represent a hydrogen atom, a straight-chain or branched C1-C5 alkyl group, a straight-chain or branched C1-C5 alkoxy group, a straight-chain or branched C2-C11 alkenyl group, a straight-chain or branched C2-C11 alkynyl group, or a phenyl group which may be substituted with 1 to 3 substituents selected from the group consisting of a halogen atom, a straight-chain or branched C1-C5 alkyl group, a straight-chain or branched C1-C5 alkoxy group, a nitro group and C1-C3 alkylenedioxy group, and $R^3$ represents a hydrogen atom or a straight-chain or branched C1-C5 alkyl group.

9. The method according to any one of claims 1 to 7, wherein $R^1$ and $R^2$ are respectively a hydrogen atom, a methyl group or a phenyl group, and $R^3$ represents a hydrogen atom or a methyl group.

* * * * *